(12) United States Patent
Radhakrishnan et al.

(10) Patent No.: US 10,758,333 B2
(45) Date of Patent: Sep. 1, 2020

(54) HIGH RESISTANCE IMPLANTED BRONCHIAL ISOLATION DEVICES AND METHODS

(71) Applicant: Pulmonx Corporation, Redwood City, CA (US)

(72) Inventors: Sri Radhakrishnan, Cupertino, CA (US); Ryan Olivera, Granite Bay, CA (US)

(73) Assignee: Pulmonx Corporation, Redwood City, CA (US)

( * ) Notice: Subject to any disclaimer, the term of this patent is extended or adjusted under 35 U.S.C. 154(b) by 0 days.

(21) Appl. No.: 15/714,868

(22) Filed: Sep. 25, 2017

(65) Prior Publication Data

US 2018/0092731 A1   Apr. 5, 2018

Related U.S. Application Data

(60) Provisional application No. 62/404,688, filed on Oct. 5, 2016.

(51) Int. Cl.
*A61F 2/04* (2013.01)
*A61B 17/12* (2006.01)
(Continued)

(52) U.S. Cl.
CPC .......... *A61F 2/04* (2013.01); *A61B 17/12036* (2013.01); *A61B 17/12104* (2013.01);
(Continued)

(58) Field of Classification Search
CPC ... A61F 2/04; A61F 2002/043; A61M 16/209; A61M 16/0406; A61M 16/208;
(Continued)

(56) References Cited

U.S. PATENT DOCUMENTS 6,694,979 B2   2/2004   Deem et al.
6,941,950 B2   9/2005   Wilson et al.
(Continued)

FOREIGN PATENT DOCUMENTS

WO   WO-2018067735 A1   4/2018

OTHER PUBLICATIONS http://www.onyxvalve.com/product/check-valves/series-dbcp/18 (Year: 2014).*

(Continued)

*Primary Examiner* — Brian A Dukert
*Assistant Examiner* — Rebecca Lynee Zimmerman
(74) *Attorney, Agent, or Firm* — Wilson Sonsini Goodrich & Rosati

(57) ABSTRACT

Disclosed are methods and devices for regulating fluid flow to and from a region of a patient's lung, such as to achieve a desired fluid flow dynamic to a lung region during respiration and/or to induce collapse in one or more lung regions. Pursuant to an exemplary procedure, an identified region of the lung is targeted for treatment. The targeted lung region is then bronchially isolated to regulate airflow into and/or out of the targeted lung region through one or more bronchial passageways that feed air to the targeted lung region. An exemplary flow control device is configured to block fluid flow in the inspiratory direction and the expiratory direction at normal breathing pressures and allow fluid flow in the expiratory direction at coughing pressures.

11 Claims, 19 Drawing Sheets

(51) Int. Cl.
*A61M 16/04* (2006.01)
*A61M 16/20* (2006.01)

(52) U.S. Cl.
CPC ... *A61B 17/12172* (2013.01); *A61M 16/0406* (2014.02); *A61M 16/209* (2014.02); *A61B 17/12177* (2013.01); *A61F 2002/043* (2013.01); *A61M 16/208* (2013.01); *A61M 2205/04* (2013.01)

(58) Field of Classification Search
CPC ......... A61M 2205/04; A61B 17/12104; A61B 17/12036; A61B 17/17172; A61B 17/12177; A61B 2017/00867; A61B 2017/00862; A61B 2017/242; A61B 17/1204
See application file for complete search history.

(56) References Cited

U.S. PATENT DOCUMENTS

| | | | |
|---|---|---|---|
| 7,011,094 B2 | 3/2006 | Rapacki et al. | |
| 8,474,460 B2 | 7/2013 | Barrett et al. | |
| 2002/0029779 A1* | 3/2002 | Schmidt | A61M 15/0086 128/205.25 |
| 2003/0050648 A1 | 3/2003 | Alferness et al. | |
| 2003/0070682 A1* | 4/2003 | Wilson | A61F 2/2412 128/207.16 |
| 2003/0070683 A1 | 4/2003 | Deem et al. | |
| 2003/0127090 A1* | 7/2003 | Gifford | A61M 16/0057 128/200.24 |
| 2004/0089306 A1 | 5/2004 | Hundertmark et al. | |
| 2006/0076023 A1 | 4/2006 | Rapacki et al. | |
| 2007/0295338 A1 | 12/2007 | Loomas et al. | |
| 2011/0226238 A1 | 9/2011 | Barrett et al. | |
| 2013/0289711 A1* | 10/2013 | Liddy | A61F 2/06 623/1.24 |

OTHER PUBLICATIONS

"International Search Report dated Jan. 2, 2018 for International PCT Patent Application No. PCT/US2017/055192.".
EESR for EP17859137 dated Apr. 30, 2020.

* cited by examiner

HIGH RESISTANCE IMPLANTED BRONCHIAL ISOLATION DEVICES AND METHODS

CROSS-REFERENCE TO RELATED APPLICATIONS

This application claims the benefit of Provisional No. 62/404,688, filed Oct. 5, 2016, the entire content of which is incorporated herein by reference.

FIELD OF THE INVENTION

This disclosure relates generally to methods and devices for use in performing pulmonary procedures and, more particularly, to procedures for treating lung diseases.

BACKGROUND OF THE INVENTION

Pulmonary diseases, such as chronic obstructive pulmonary disease, (COPD), reduce the ability of one or both lungs to fully expel air during the exhalation phase of the breathing cycle. Such diseases are accompanied by chronic or recurrent obstruction to air flow within the lung. Because of the increase in environmental pollutants, cigarette smoking, and other noxious exposures, the incidence of COPD has increased dramatically in the last few decades and now ranks as a major cause of activity-restricting or bed-confining disability in the United States. COPD can include such disorders as chronic bronchitis, bronchiectasis, asthma, and emphysema.

It is known that emphysema and other pulmonary diseases reduce the ability of one or both lungs to fully expel air during the exhalation phase of the breathing cycle. One of the effects of such diseases is that the diseased lung tissue is less elastic than healthy lung tissue, which is one factor that prevents full exhalation of air. During breathing, the diseased portion of the lung does not fully recoil due to the diseased (e.g., emphysematic) lung tissue being less elastic than healthy tissue.

Consequently, the diseased lung tissue exerts a relatively low driving force, which results in the diseased lung expelling less air volume than a healthy lung. The reduced air volume exerts less force on the airway, which allows the airway to close before all air has been expelled, another factor that prevents full exhalation.

The problem is further compounded by the diseased, less elastic tissue that surrounds the very narrow airways that lead to the alveoli, which are the air sacs where oxygen-carbon dioxide exchange occurs. The diseased tissue has less tone than healthy tissue and is typically unable to maintain the narrow airways open until the end of the exhalation cycle. This traps air in the lungs and exacerbates the already-inefficient breathing cycle. The trapped air causes the tissue to become hyper-expanded and no longer able to effect efficient oxygen-carbon dioxide exchange.

In addition, hyper-expanded, diseased lung tissue occupies more of the pleural space than healthy lung tissue. In most cases, a portion of the lung is diseased while the remaining part is relatively healthy and, therefore, still able to efficiently carry out oxygen exchange. By taking up more of the pleural space, the hyper-expanded lung tissue reduces the amount of space available to accommodate the healthy, functioning lung tissue. As a result, the hyper-expanded lung tissue causes inefficient breathing due to its own reduced functionality and because it adversely affects the functionality of adjacent healthy tissue.

Some recent treatments include the use of devices that isolate a diseased region of the lung in order to reduce the volume of the diseased region, such as by collapsing the diseased lung region. According to such treatments, one or more flow control devices are implanted in airways feeding a diseased region of the lung to regulate fluid flow to the diseased lung region in order to fluidly isolate the region of the lung. These implanted flow control devices can be, for example, one-way valves that allow flow in the exhalation direction only, occluders or plugs that prevent flow in either direction, or two-way valves that control flow in both directions. However, such devices are still in the development stages.

Thus, there is much need for improvement in the design and functionality of such flow control devices.

BRIEF SUMMARY OF THE INVENTION

Disclosed are methods and devices for regulating fluid flow to and from a region of a patient's lung, such as to achieve a desired fluid flow dynamic to a lung region during respiration and/or to induce collapse in one or more lung regions. In one aspect, a flow control device suitable for implanting in a bronchial passageway is described. The flow control device comprises a valve element comprising a first lip and a second lip, wherein the first and second lips are configured to transition the valve element between a closed configuration that blocks air flow in the inspiratory direction and an open configuration that permits air flow in an expiratory direction. The first and second lips are configured to be in the closed configuration when exposed to no air flow, air flow in the inspiratory direction, and air flow in the expiratory direction at normal breathing pressures. The first and second lips are additionally configured to be in the open configuration when exposed to air flow in the expiratory direction at coughing pressures.

In an embodiment, the first and second lips are configured to be parallel with respect to one another in the closed configuration. The valve element may further comprise two opposed inclined flaps leading to the first and second lips, wherein the two inclined flaps are oriented at an angle with respect to one another. The angle may be in the range of 70 to 110 degrees. The first and second lips may be configured to be parallel with a longitudinal axis of the valve while in the closed configuration. The two inclined flaps may be oriented at an angle relative to a longitudinal axis of the valve while in the closed configuration. In an embodiment, the valve is configured to have a cracking pressure in the range of 5-25 inches $H_2O$. In another embodiment, the valve is configured to have a cracking pressure in the range of 7-9 inches $H_2O$. In an embodiment, the flow control device may further comprise a frame configured to retain the flow control device within the bronchial passageway and a seal coupled to the frame. The seal may be configured to seal against internal walls of the bronchial passageway.

In one aspect, the flow control device comprises a valve comprising coaptation regions comprising two opposed inclined flaps and two parallel lips connected to the inclined flaps, wherein the coaptation regions are configured to transition the valve element between a closed configuration that blocks air flow in the inspiratory direction and an open configuration that permits air flow in an expiratory direction. The coaptation regions are configured to be in the closed configuration when exposed to no air flow, air flow in the inspiratory direction, and air flow in the expiratory direction at normal breathing pressures, and wherein the coaptation regions are configured to be in the open configuration when exposed to air flow in the expiratory direction at coughing pressures.

This and other aspects of the present disclosure are described herein.

BRIEF DESCRIPTION OF THE DRAWINGS

Present embodiments have other advantages and features which will be more readily apparent from the following detailed description and the appended claims, when taken in conjunction with the accompanying drawings, in which:

DETAILED DESCRIPTION OF THE INVENTION

Figure 1:
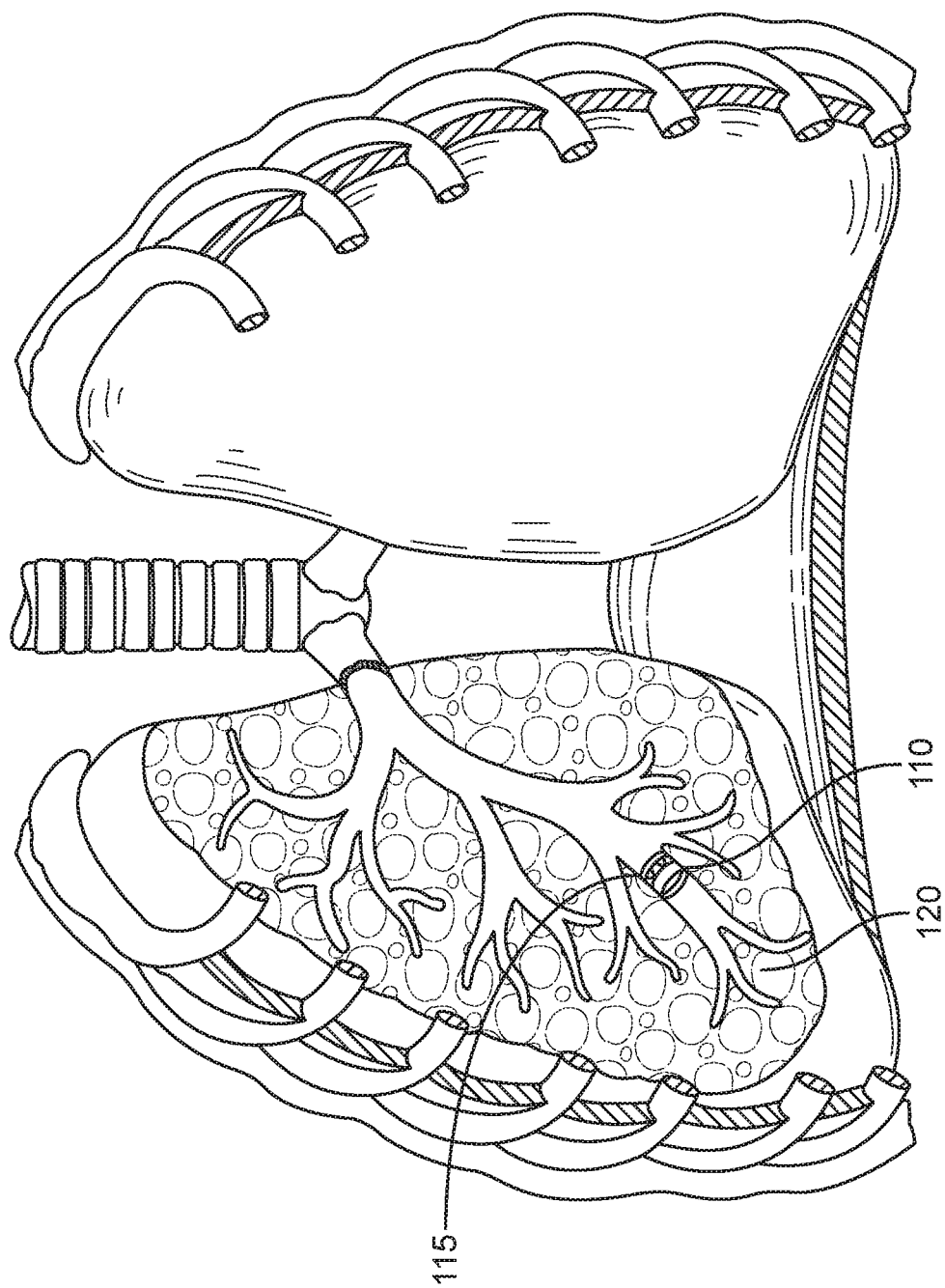
FIG. 1 shows an anterior view of a pair of human lungs and a bronchial tree with a flow control device implanted in a bronchial passageway to bronchially isolate a region of the lung.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

Disclosed are methods and devices for regulating fluid flow to and from a region of a patient's lung, such as to achieve a desired fluid flow dynamic to a lung region during respiration and/or to induce collapse in one or more lung regions. Pursuant to an exemplary procedure, an identified region of the lung (referred to herein as the "targeted lung region") is targeted for treatment. The targeted lung region is then bronchially isolated to regulate airflow into and/or out of the targeted lung region through one or more bronchial passageways that feed air to the targeted lung region.

As shown in FIG. 1, the bronchial isolation of the targeted lung region is accomplished by implanting a flow control device 110 (sometimes referred to as a bronchial isolation device) into a bronchial passageway 115 that feeds air to a targeted lung region 120. The flow control device 110 regulates fluid flow through the bronchial passageway 115 in which the flow control device 110 is implanted. The flow control device 110 can regulate airflow through the bronchial passageway 115 using a valve that permits fluid flow in a first direction (e.g., the exhalation direction) while limiting or preventing fluid flow in a second direction (e.g., the inhalation direction).

The valve includes coaptation regions that are moveable toward and away from one another so as to define an opening through which fluid can flow. When exposed to fluid flow with sufficient pressure in the first direction (e.g., the exhalation direction), the coaptation regions are urged away from one another permit fluid flow through the valve. When exposed to fluid flow in the second direction (e.g., the inhalation direction), the coaptation regions are urged toward one another to decrease the size of and/or completely close the opening to decrease and/or completely prevent fluid flow through the valve. Flow through the valve is completely prevented when the coaptation regions are completely shut such that there is no opening for fluid to flow through the valve.

As described in detail below, the flow control device 110 can include a valve that is closed in a default state such that there is no gap or opening between the coaptation regions of the valve. The coaptation regions separate from one another to form an opening for fluid flow in the first direction when the valve cracking pressure is exceeded. For such a valve, there is a tendency for the coaptation regions, such as the valve lips, to stick together so as to resist opening and thereby increase the valve cracking pressure. The sticking force between the coaptation regions can be stronger when the valve is implanted in a lung, as mucous can coat the valve lips and form surface tension that must be overcome to separate the lips and open the valve.

Throughout this disclosure, reference is made to the term "lung region". As used herein, the term "lung region" refers to a defined division or portion of a lung. For purposes of example, lung regions are described herein with reference to human lungs, wherein some exemplary lung regions include lung lobes and lung segments. Thus, the term "lung region" as used herein can refer, for example, to a lung lobe or a lung segment. Such nomenclature conform to nomenclature for portions of the lungs that are known to those skilled in the art. However, it should be appreciated that the term "lung region" does not necessarily refer to a lung lobe or a lung segment, but can refer to some other defined division or portion of a human or nonhuman lung.

Figure 2:
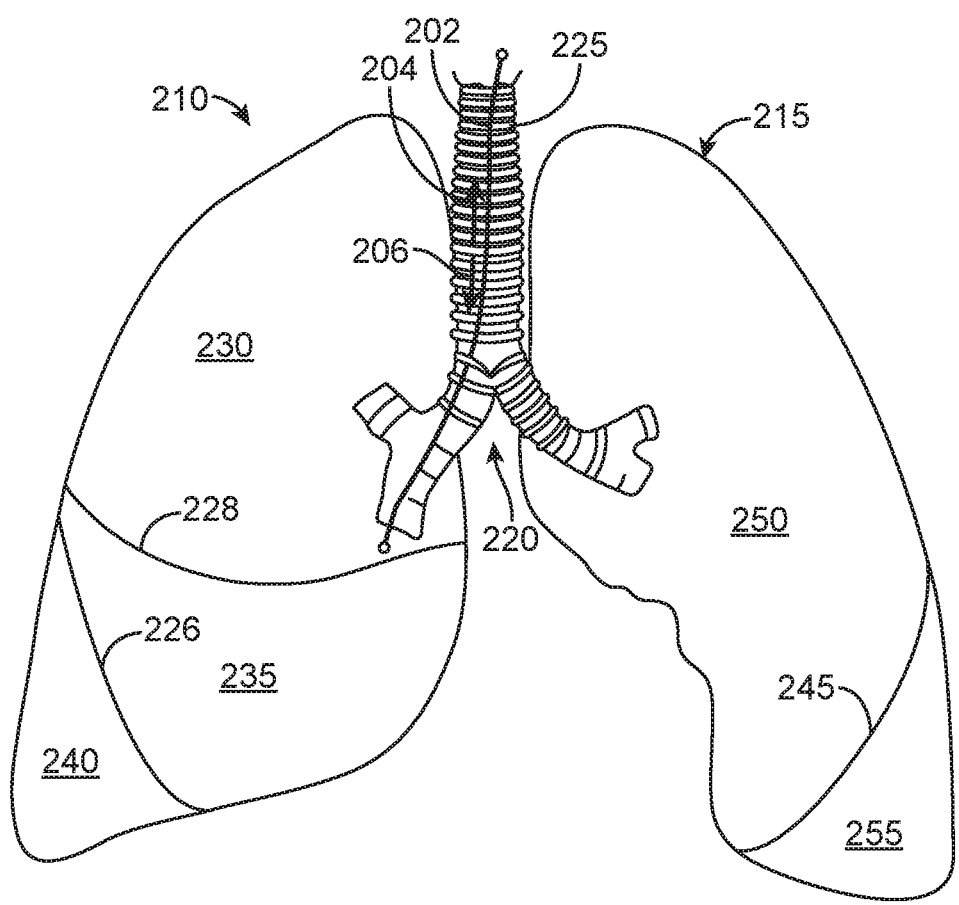
FIG. 2 illustrates an anterior view of a pair of human lungs and a bronchial tree
Figure 5A:
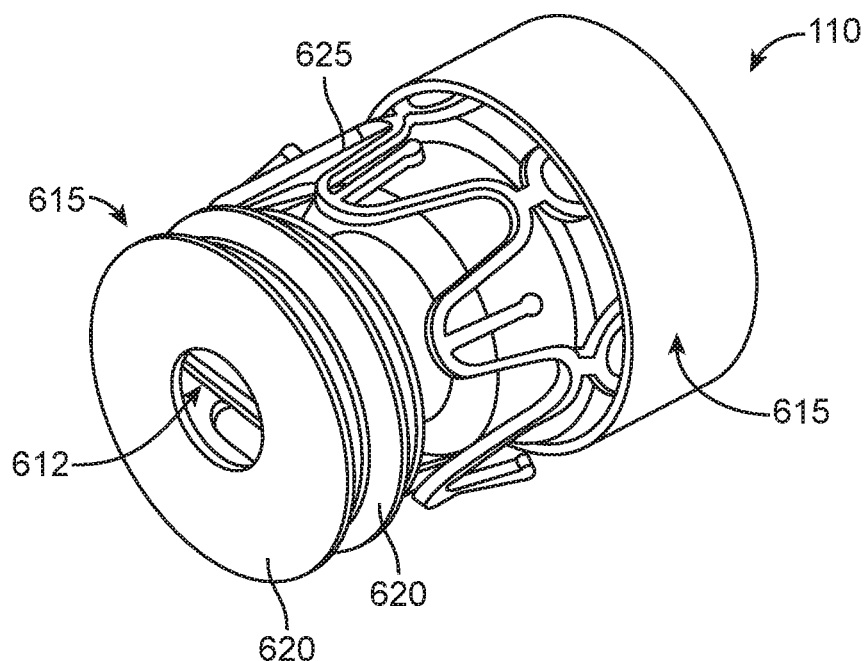
FIG. 5A shows a perspective view of an exemplary flow control device that can be implanted in a body passageway.

FIG. 2 shows an anterior view of a pair of human lungs 210, 215 and a bronchial tree 220 that provides a fluid pathway into and out of the lungs 210, 215 from a trachea 225, as will be known to those skilled in the art. As used herein, the term "fluid" can refer to a gas, a liquid, or a combination of gas(es) and liquid(s). For clarity of illustration, FIG. 2 shows only a portion of the bronchial tree 220, which is described in more detail below with reference to FIG. 5.

Throughout this description, certain terms are used that refer to relative directions or locations along a path defined from an entryway into the patient's body (e.g., the mouth or nose) to the patient's lungs. The path of airflow into the lungs generally begins at the patient's mouth or nose, travels through the trachea into one or more bronchial passageways, and terminates at some point in the patient's lungs. For example, FIG. 2 shows a path 202 that travels through the trachea 225 and through a bronchial passageway into a location in the right lung 210. The term "proximal direction" refers to the direction along such a path 202 that points toward the patient's mouth or nose and away from the patient's lungs. In other words, the proximal direction is generally the same as the expiration direction when the patient breathes. The arrow 204 in FIG. 2 points in the proximal or expiratory direction. The term "distal direction" refers to the direction along such a path 202 that points toward the patient's lung and away from the mouth or nose. The distal direction is generally the same as the inhalation or inspiratory direction when the patient breathes. The arrow 206 in FIG. 2 points in the distal or inhalation direction.

The lungs include a right lung 210 and a left lung 215. The right lung 210 includes lung regions comprised of three lobes, including a right upper lobe 230, a right middle lobe 235, and a right lower lobe 240. The lobes 230, 235, 240 are separated by two interlobar fissures, including a right oblique fissure 226 and a right transverse fissure 228. The right oblique fissure 226 separates the right lower lobe 240 from the right upper lobe 230 and from the right middle lobe 235. The right transverse fissure 228 separates the right upper lobe 230 from the right middle lobe 235.

As shown in FIG. 2, the left lung 215 includes lung regions comprised of two lobes, including the left upper lobe 250 and the left lower lobe 255. An interlobar fissure comprised of a left oblique fissure 245 of the left lung 215 separates the left upper lobe 250 from the left lower lobe 255. The lobes 230, 235, 240, 250, 255 are directly supplied air via respective lobar bronchi, as described in detail below.

Figure 3A:
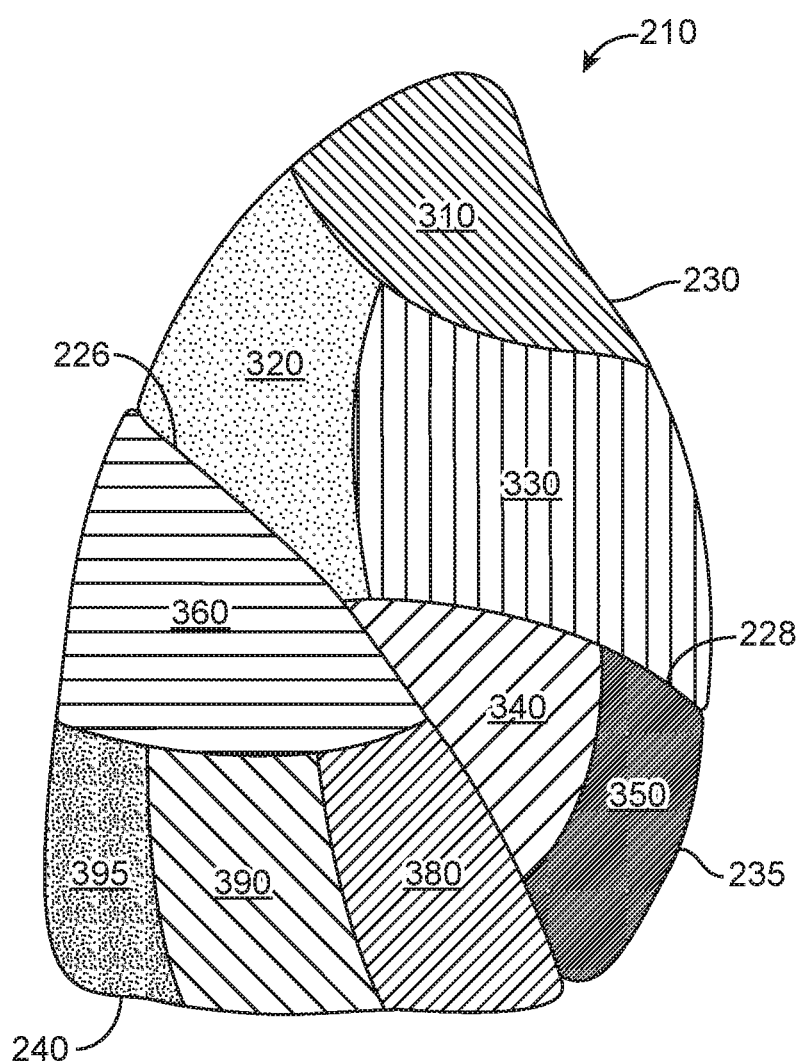
FIG. 3A illustrates a lateral view of the right lung.

FIG. 3A is a lateral view of the right lung 210. The right lung 210 is subdivided into lung regions comprised of a plurality of bronchopulmonary segments. Each bronchopulmonary segment is directly supplied air by a corresponding segmental tertiary bronchus, as described below. The bronchopulmonary segments of the right lung 210 include a right apical segment 310, a right posterior segment 320, and a right anterior segment 330, all of which are disposed in the right upper lobe 230. The right lung bronchopulmonary segments further include a right lateral segment 340 and a right medial segment 350, which are disposed in the right middle lobe 235. The right lower lobe 240 includes bronchopulmonary segments comprised of a right superior segment 360, a right medial basal segment (which cannot be seen from the lateral view and is not shown in FIG. 3A), a right anterior basal segment 380, a right lateral basal segment 390, and a right posterior basal segment 395.

Figure 3B:
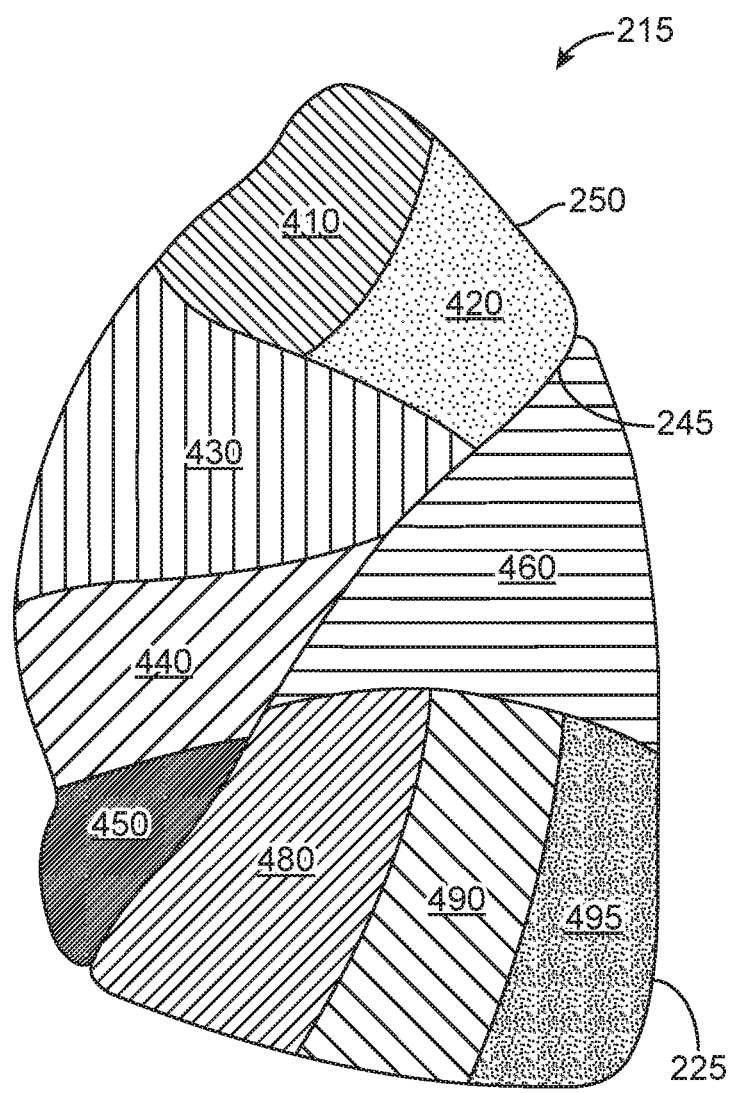
FIG. 3B illustrates a lateral view of the left lung.

FIG. 3B shows a lateral view of the left lung 215, which is subdivided into lung regions comprised of a plurality of bronchopulmonary segments. The bronchopulmonary segments include a left apical segment 410, a left posterior segment 420, a left anterior segment 430, a left superior segment 440, and a left inferior segment 450, which are disposed in the left lung upper lobe 250. The lower 15 lobe 225 of the left lung 215 includes bronchopulmonary segments comprised of a left superior segment 460, a left medial basal segment (which cannot be seen from the lateral view and is not shown in FIG. 3B), a left anterior basal segment 480, a left lateral basal segment 490, and a left posterior basal segment 495.

Figure 4:
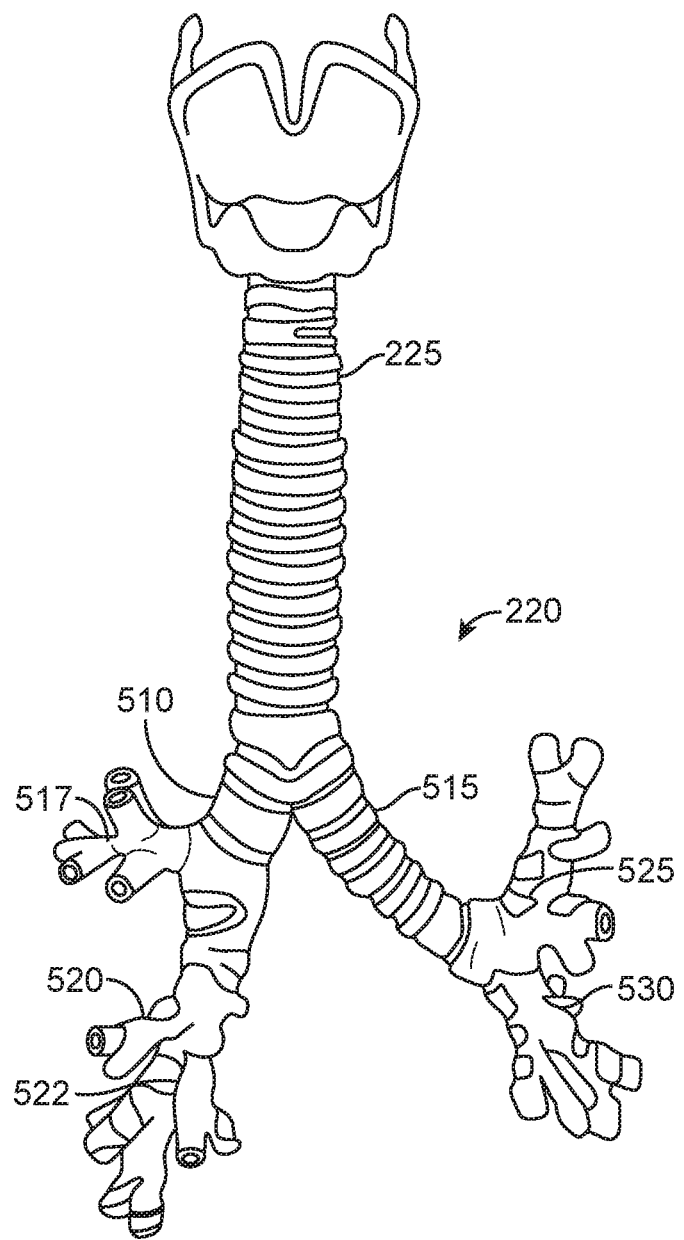
FIG. 4 illustrates an anterior view of the trachea and a portion of the bronchial tree.

FIG. 4 shows an anterior view of the trachea 225 and a portion of the bronchial tree 220, which includes a network of bronchial passageways, as described below. In the context of describing the lung, the terms "pathway" and "lumen" are used interchangeably herein. The trachea 225 divides at a lower end into two bronchial passageways comprised of primary bronchi, including a right primary bronchus 510 that provides direct air flow to the right lung 210, and a left primary bronchus 515 that provides direct air flow to the left lung 215. Each primary bronchus 510, 515 divides into a next generation of bronchial passageways comprised of a plurality of lobar bronchi. The right primary bronchus 510 divides into a right upper lobar bronchus 517, a right middle lobar bronchus 520, and a right lower lobar bronchus 522. The left primary bronchus 515 divides into a left upper lobar bronchus 525 and a left lower lobar bronchus 530. Each lobar bronchus, 517, 520, 522, 525, 530 directly feeds fluid to a respective lung lobe, as indicated by the respective names of the lobar bronchi. The lobar bronchi each divide into yet another generation of bronchial passageways comprised of segmental bronchi, which provide air flow to the bronchopulmonary segments discussed above.

As is known to those skilled in the art, a bronchial passageway defines an internal lumen through which fluid can flow to and from a lung or lung region. The diameter of the internal lumen for a specific bronchial passageway can vary based on the bronchial passageway's location in the bronchial tree (such as whether the bronchial passageway is a lobar bronchus or a segmental bronchus) and can also vary from patient to patient. However, the internal diameter of a bronchial passageway is generally in the range of 3 millimeters (mm) to 10 mm, although the internal diameter of a bronchial passageway can be outside of this range. For example, a bronchial passageway can have an internal diameter of well below 1 mm at locations deep within the lung.

Flow Control Device. Some of the breathing patterns that are characteristic of patients with severe emphysema are that the patients are able to inhale very easily and yet exhale with great difficulty. The destruction of lung parenchyma in the diseased regions of the lung leads to a loss of elastic recoil for the diseased lung region. The resulting imbalance in elastic recoil between diseased and healthier lung regions results in the diseased lung regions filling with air easily and first during inspiration. However, the diseased regions empty last and with great difficulty during expiration, as there is little or no elastic recoil remaining in the diseased lung regions to assist in the expelling of air. Adding to this difficulty, the distal airways in the diseased lung regions collapse during exhalation due to the loss of tethering forces that hold the airways open during exhalation in normal lung regions. As pleural pressure increases at the beginning of expiration, these distal airways partially or fully collapse, thus decreasing the exhalation flow, and increasing the work and time required for the patient to fully exhale.

To help ease the symptoms of emphysema and to improve breathing mechanics, implantation of one-way flow control devices or valve bronchial isolation devices has been employed, as described in several prior U.S. patent applications, including "Methods and Devices for use in Performing Pulmonary Procedures", Ser. No. 09/797,910, filed Mar. 2, 2001, "Bronchial Flow Control Devices and Methods of Use", Ser. No. 10/270,792, filed Oct. 10, 2002, and "Implanted Bronchial Isolation Devices And Methods", Ser. No. 12/885,199, filed Sep. 17, 2010 which are incorporated herein by reference.

FIGS. 5A-6B show an exemplary embodiment of a flow control device 110 that generally includes a valve, a frame or anchor, and a seal member for sealing against a wall of a bronchial passageway. It should be appreciated that the flow control device 110 shown in FIGS. 5A-6B is exemplary and that the frame, seal member, and valve can vary in structure. The flow control device 110 has a general outer shape and contour that permits the flow control device 110 to fit entirely or at least partially within a body passageway, such as within a bronchial passageway.

The valve is configured to regulate fluid flow through a bronchial passageway in which the device 110 is implanted. The valve opens and vents fluid (such as gas or liquid, including mucous) when the pressure across the valve due to flow in a first direction, such as the exhalation direction, exceeds the rated cracking pressure of the valve. Thus, the valve opens in response to fluid flow in the first direction. The valve moves towards a closed configuration in response to fluid flow in a second, opposite direction such as the inhalation direction.

Figure 5B:
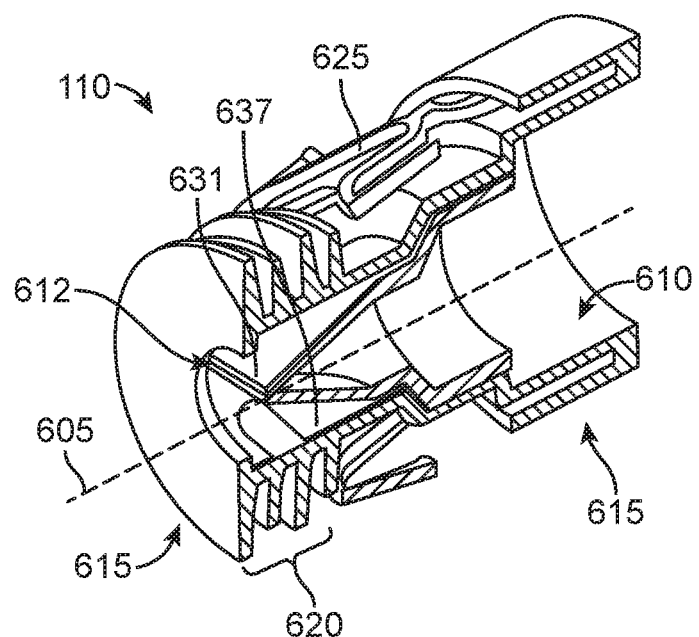
FIG. 5B shows a perspective, cross-sectional view of the flow control device of FIG. 5A.
Figure 6A:
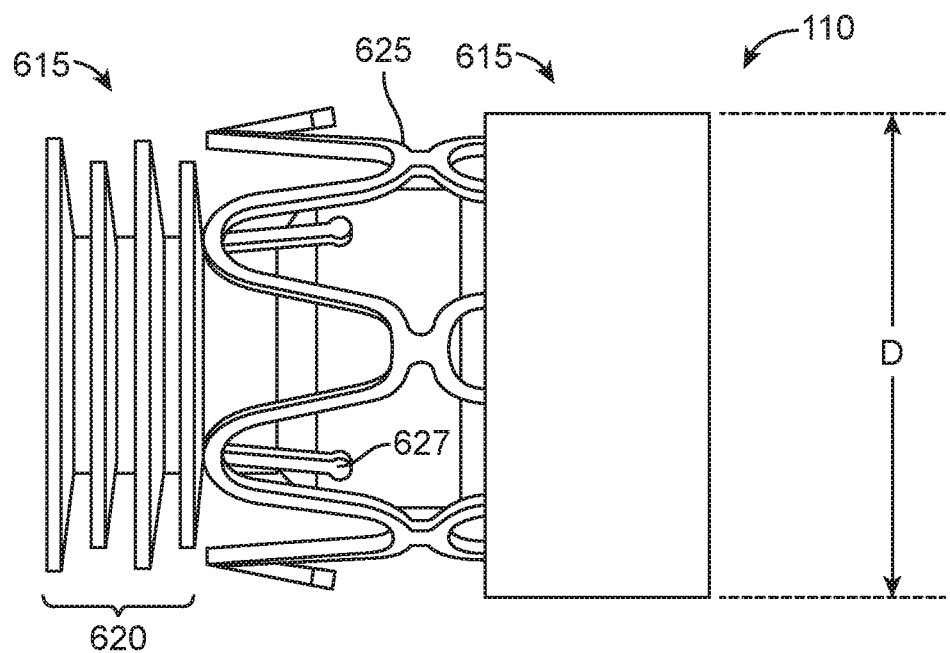
FIG. 6A shows a side view of the flow control device of FIG. 5A.
Figure 6B:
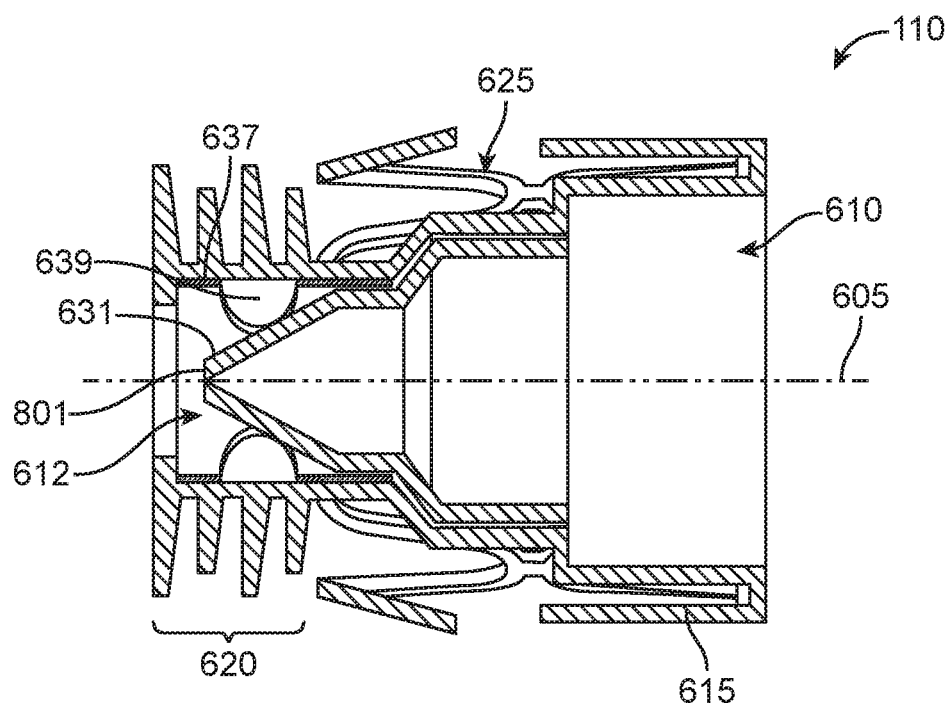
FIG. 6B shows a cross-sectional, side view of the flow control device of FIG. 5A.

With reference to FIGS. 5A-6B, the flow control device 110 extends generally along a central axis 605 (shown in FIGS. 5B and 6B). The flow control device 110 includes a main body that defines an interior lumen 610 through which fluid can flow along a flow path. The dimensions of the flow control device 110 can vary based upon the bronchial passageway in which the flow control device 110 is configured to be implanted. The valve does not have to be precisely sized for the bronchial passageway it is to be placed within. Generally, the diameter D (shown in FIG. 6A) of the flow control device 110 in the uncompressed state is larger than the inner diameter of the bronchial passageway in which the flow control device 110 will be placed. This will permit the flow control device 110 to be compressed prior to insertion in the bronchial passageway and then expand upon insertion in the bronchial passageway, which will provide for a secure fit between the flow control device 110 and the bronchial passageway.

The flow of fluid through the interior lumen 610 is controlled by a valve 612 that is disposed at a location along the interior lumen such that fluid must flow through the valve 612 in order to flow through the interior lumen 610. It should be appreciated that the valve 612 could be positioned at various locations along the interior lumen 610. The valve 612 can be made of a biocompatible material, such as a biocompatible polymer, such as silicone. As discussed in more detail below, the configuration of the valve 612 can vary based on a variety of factors, such as the desired cracking pressure of the valve 612.

The valve 612 can be configured to permit fluid to flow in only one-direction through the interior lumen 610, to permit regulated flow in two-directions through the interior lumen 610, or to prevent fluid flow in either direction.

With reference still to FIGS. 5A-6B, the flow control device 110 includes a seal member 615 that provides a seal with the internal walls of a body passageway when the flow control device is implanted into the body passageway. The seal member 615 is manufactured of a deformable material, such as silicone or a deformable elastomer. The flow control device 110 also includes an anchor member or frame 625 that functions to anchor the flow control device 110 within a body passageway.

As shown in FIGS. 5A-6B, the seal member 615 can includes a series of radially-extending, circular flanges 620 that surround the outer circumference of the flow control device 110. The configuration of the flanges can vary. For example, as shown in FIG. 6B, the radial length of each flange 620 can vary. It should be appreciated that the radial length could be equal for all of the flanges 620 or that the radial length of each flange could vary in some other manner. In addition, the flanges 620 can be oriented at a variety of angles relative to the longitudinal axis 605 of the flow control device.

As mentioned, the anchor member 625 functions to anchor the flow control device 110 in place when the flow control device is implanted within a body passageway, such as within a bronchial passageway. The anchor member 625 has a structure that can contract and expand in size (in a radial direction and/or in a longitudinal direction) so that the anchor member can expand to grip the interior walls of a body passageway in which the flow control device is positioned. In one embodiment, as shown in FIGS. 5A-6B, the anchor member 625 comprises an annular frame that surrounds the flow control device 110.

The frame 625 can be formed from a super-elastic material, such as Nickel Titanium (also known as Nitinol), such as by cutting the frame out of a tube of Nitinol or by forming the frame out of Nitinol wire. The super-elastic properties of Nitinol can result in the frame exerting a radial force against the interior walls of a bronchial passageway sufficient to anchor the flow control device 110 in place.

It should be appreciated that the configurations, including the sizes and shapes, of the frame 625 and the seal member 615 can vary from those shown in the figures. The seal 615 and/or the frame 625 can contract or expand in size, particularly in a radial direction. The default state is an expanded size, such that the flow control device 110 will have a maximum diameter (which is defined by either the seal 615 or the frame 625) when the flow control device 110 is in the default state. The flow control device 110 can be radially contracted in size during insertion into a bronchial passageway, so that once the flow control device 110 is inserted into the passageway, it expands within the passageway.

At least a portion of the valve 612 is optionally surrounded by a rigid or semirigid valve protector member 637 (shown in FIGS. 5B and 6B), which is a tubular member or annular wall that is contained inside the seal member 615. In another embodiment, the valve protector can comprise a coil of wire or a ring of wire that provides some level of structural support to the flow control device. The valve protector 637 can be concentrically located within the seal member 615. Alternately, the valve 612 can be completely molded within the seal member 615 such that the material of the seal member 615 completely surrounds the valve protector. The valve protector has sufficient rigidity to maintain the shape of the valve member against compression.

In one embodiment, the valve protector member 637 has two or more windows 639 comprising holes that extend through the valve protector member, as shown in FIG. 6B. The windows 639 can provide a location where a removal device, such as graspers or forceps, can be inserted in order to facilitate removal of the flow control device 110 from a bronchial passageway.

Figure 7:
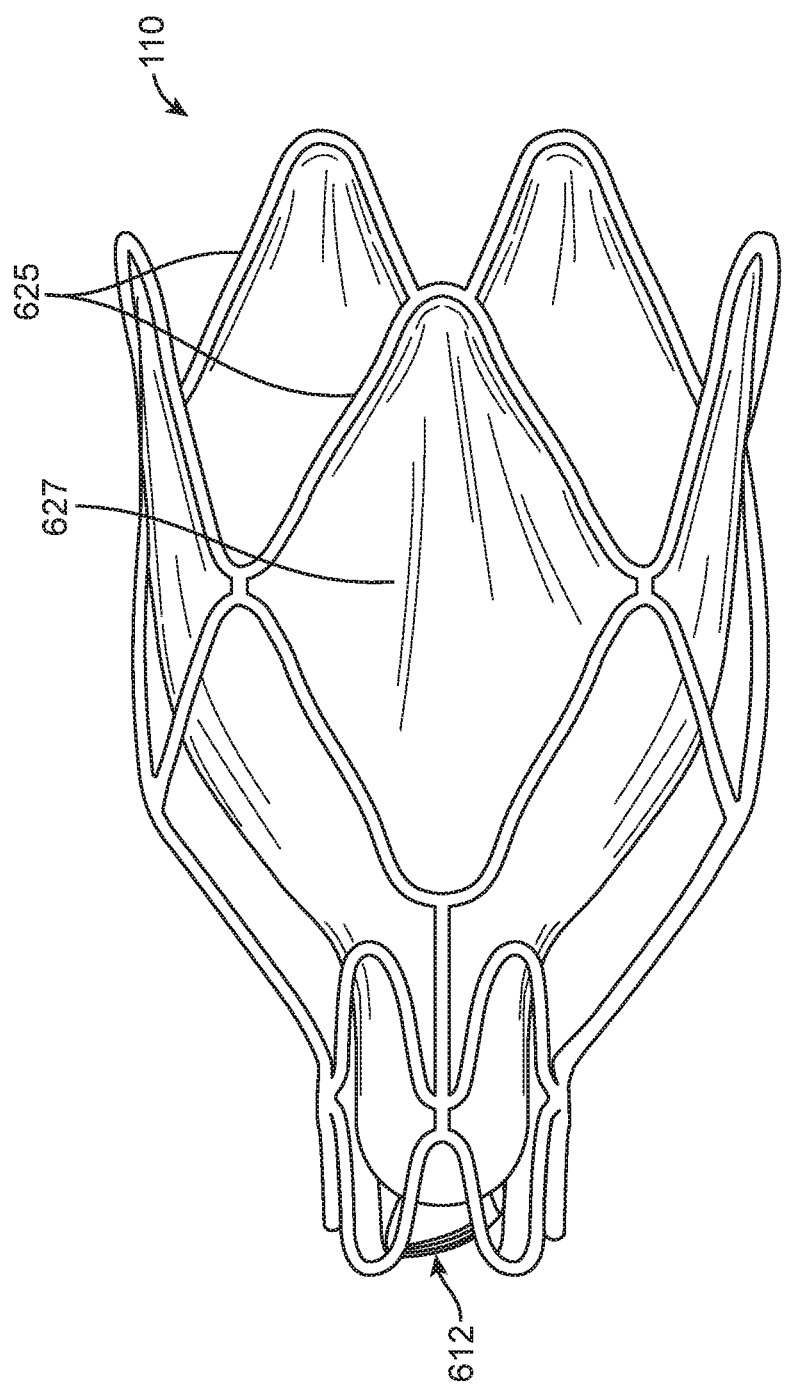
FIG. 7 shows another embodiment of a flow control device.

As mentioned, the structural configuration of the flow control device can vary. For example, FIG. 7 shows a perspective view of another embodiment of a flow control device 110 that includes a frame 625, a valve 612 mounted in the frame 625, and a membrane 627. The frame 625 and the membrane 627 can collectively or individually seal with an internal wall of a bronchial passageway.

The device 110 in FIG. 7 includes an elastically expandable frame 625 that is covered with an elastomeric membrane 627. In one embodiment, the device has an expanded frame laser-cut from nitinol tubing that has been expanded and heat treated to set it in the shape shown. The frame 625 is dipped in a silicone dispersion so that all outer surfaces are covered in a thin silicone membrane.

When the device is compressed into a delivery catheter, it may be delivered through the trachea, using any of a number of well-known delivery methods, to the target bronchial lumen, and released from the catheter. Once released, the device expands and grips the walls of the bronchial lumen, and due to the silicone membrane, blocks fluid (gas and liquid) flow through the lumen in both the inhalation and exhalation directions. The frame 625 can have points or prongs on the distal end to prevent migration of the device in the distal or inhalation direction.

Of course, the frame may be made of other materials and take other shapes, may be deformable or heat expandable rather than spring resilient, and the membrane may be formed from other materials (such as urethane) and may be manufactured using methods other than dipping. This particular device is compact enough to fit into a delivery catheter that can fit through the working channel of a bronchoscope that has an internal diameter of 2.2 mm, however it may be delivered using other methods.

As discussed above, exemplary implantable one-way valve flow control devices are shown in FIG. 5A-7. A valve of a flow control device includes regions (referred to herein as coaptation regions) that contact one another to block flow through the valve, and separate from one another to allow flow through the valve. The coaptation regions can contact one another along their entire length or area such that there is no gap between therebetween and the valve is completely closed.

The valve coaptation regions may be in full contact with one another in a default state, such as when there is no pressure differential across the valve. That is, the coaptation regions are in contact with one another such that there is no opening for fluid to flow through. As mentioned, the default state is the state of the valve when exposed to no fluid flow and, therefore, no pressure differential across the valve. When a valve is "closed" the valve coaptation regions contact one another so as to block flow through the valve when there is no pressure differential across the valve.

Figure 8A:
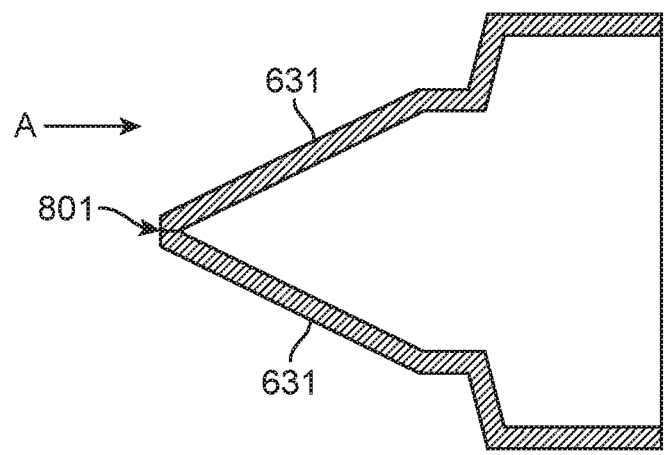
FIG. 8A shows a side, cross-sectional view of a duckbill valve in a closed state.
Figure 8B:
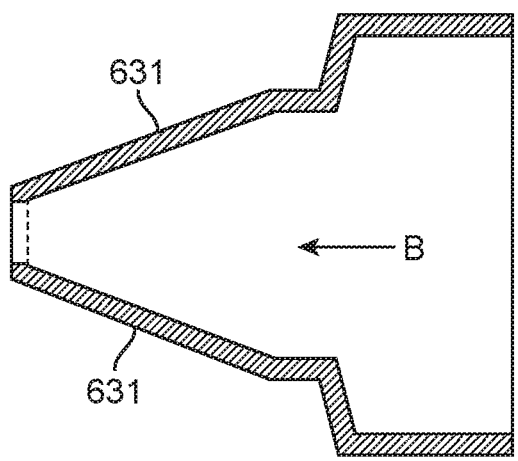
FIG. 8B shows a side, cross-sectional view of a duckbill valve in an open state.

The valve member 612 can be any type of fluid valve, and preferably is a valve that enables the cracking pressures described herein. The valve member 612 can have a smaller diameter than the frame 625 so that compression or deformation of the frame 625 in both a radial and axial direction will have little or no impact on the structure of the valve member 612. In the embodiment shown in FIGS. 5-7, the valve member 612 comprises a duckbill valve that includes two flaps 631 (shown in FIGS. 5B and 6B) that are oriented at an angle with respect to one another and that can open and close with respect to one another so as to form an opening at a lip 801 (FIG. 6B) where the flaps 631 touch one another. The duckbill valve allows fluid flow in a first direction and prevents fluid flow in a second direction that is opposed to the first direction. For example, FIG. 8A shows a schematic side-view of a duckbill valve in a closed state, wherein the flaps 631 touch one another at the lip 801. In the closed state, the duckbill valve prevents fluid flow in a first direction, which is represented by the arrow A in FIG. 8A. However, when exposed to fluid flow with sufficient pressure in a second direction (represented by arrow B in FIG. 8B) that is opposed to the first direction, the flaps 631 separate from one another to form an opening between the flaps 631 that permits flow in the second direction, as shown in FIG. 8B.

The cracking pressure is defined as the minimum fluid pressure necessary to open the one-way valve member in a certain direction, such as in the distal-to-proximal direction. Given that the valve member of the flow control device 110 will be implanted in a bronchial lumen of the human lung, the flow control device 110 will likely be coated with mucus and fluid at all times. For this reason, the cracking pressure of the valve is desirably tested in a wet condition that simulates the conditions of a bronchial lumen. A representative way of testing the valve member is to use a small amount of a water based lubricant to coat the valve mouth. The testing procedure for a duckbill valve is as follows: 1. Manually open the mouth of the valve member, such as by pinching the sides of the valve together, and place a drop of a dilute water based lubricant between the lips of the valve. 2. Wipe excess lubricant off of the valve, and force 1 cubic centimeter of air through the valve in the forward direction to push out any excess lubricant from the inside of the valve. 3. Connect the distal side of the valve to an air pressure source, and slowly raise the pressure. The pressure is increased from a starting pressure of 0 inches $H_2O$ up to a maximum of 10 inches $H_2O$ over a period of time (such as 3 seconds), and the peak pressure is recorded. This peak pressure represents the cracking pressure of the valve.

The cracking pressure of the valve member can vary based on various physiological conditions. For example, the cracking pressure could be set relative to a coughing pressure or a normal respiration pressure. For example, the cracking pressure could be set so that it is higher than normal respiration pressure and lower than a coughing pressure (approximately 25 inches $H_2O$). In this regard, the normal or coughing respiration pressure can be determined based on a particular patient, or it could be determined based on average normal or coughing respiration pressures. In one embodiment, the cracking pressure of the valve member is in the range of approximately 5-25 inches $H_2O$. In another embodiment, the cracking pressure of the valve is in the range of approximately 7-9 inches $H_2O$.

It may be desirable to have a valve with a cracking pressure above normal breathing pressures in order to reduce the risk of the targeted lung region collapsing too quickly. Thus, the cracking pressure may be set such that the valve will not open with an exhale but will open with a cough. Such a valve will act like a plug during normal breathing but will allow mucus to pass during a cough.

Figure 9:
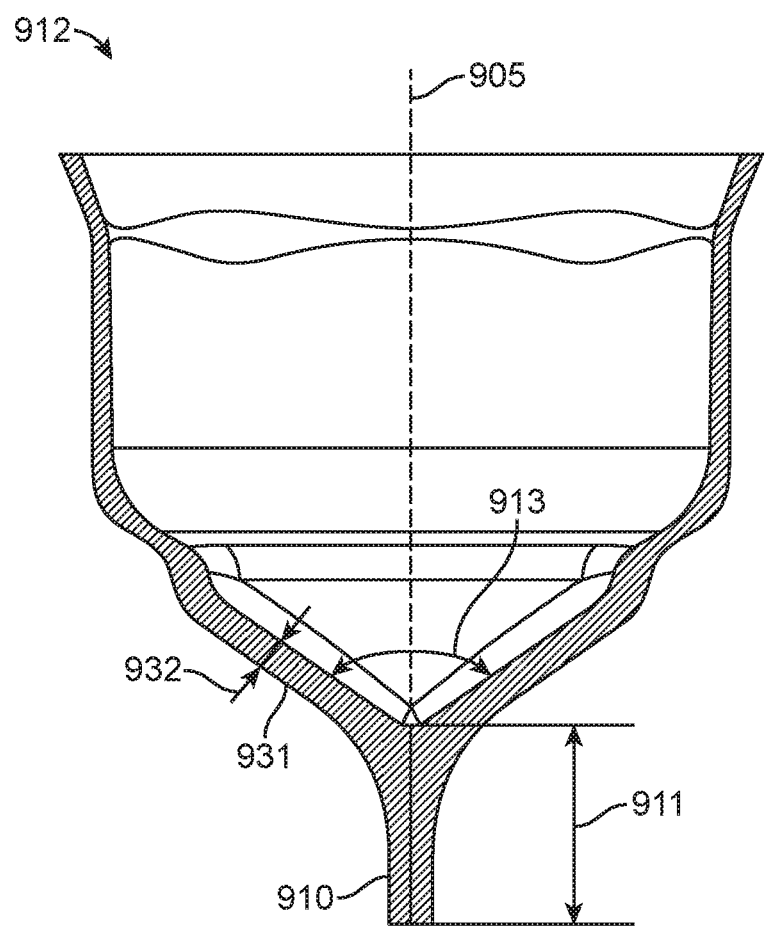
FIG. 9 shows a side, cross-sectional view of a duckbill valve with a cracking pressure above normal breathing pressures.
Figure 10A:
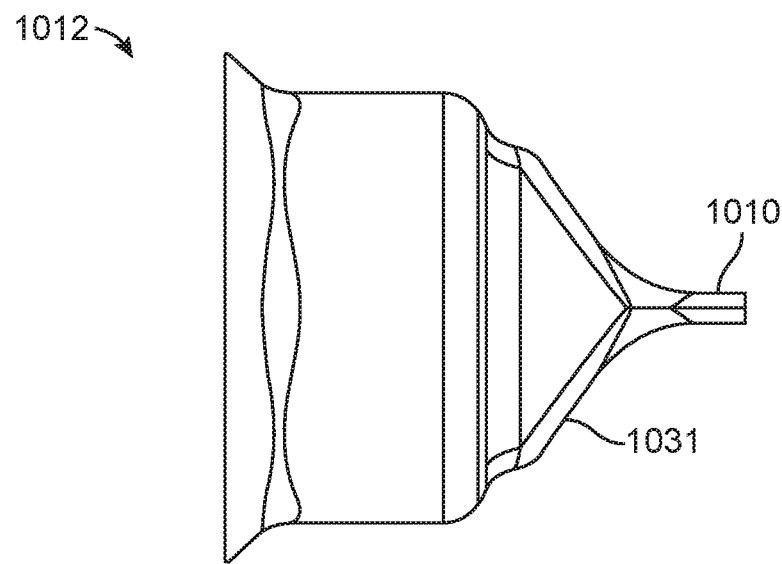
FIGS. 10A-E show an exemplary duckbill valve with a cracking pressure above normal breathing pressures.
Figure 10B:
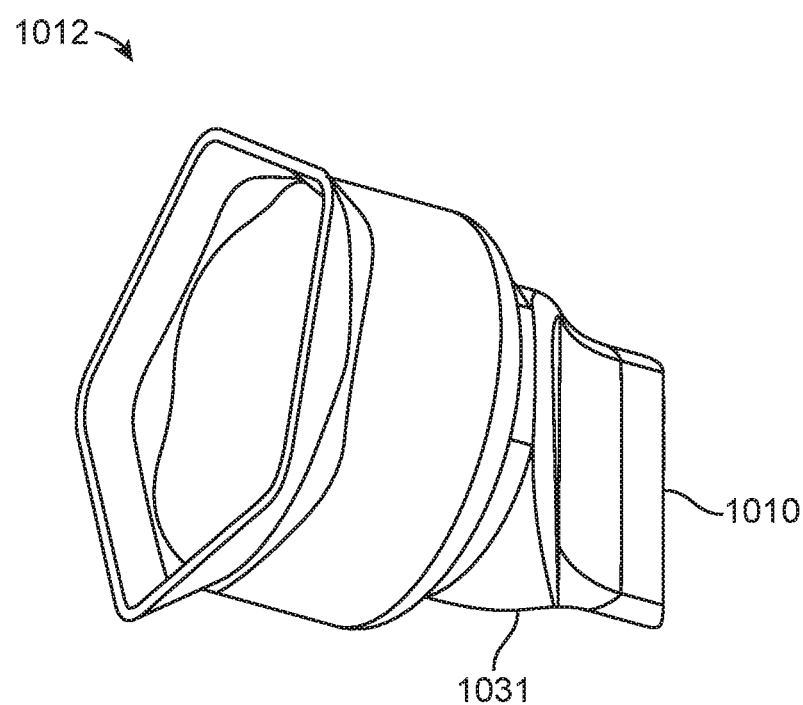
Figure 10C:
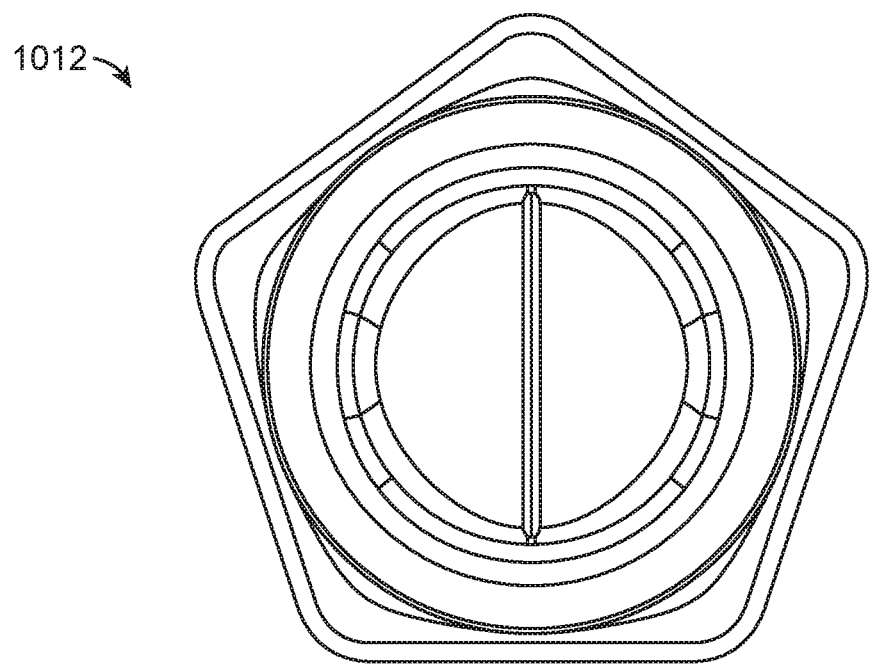
Figure 10D:
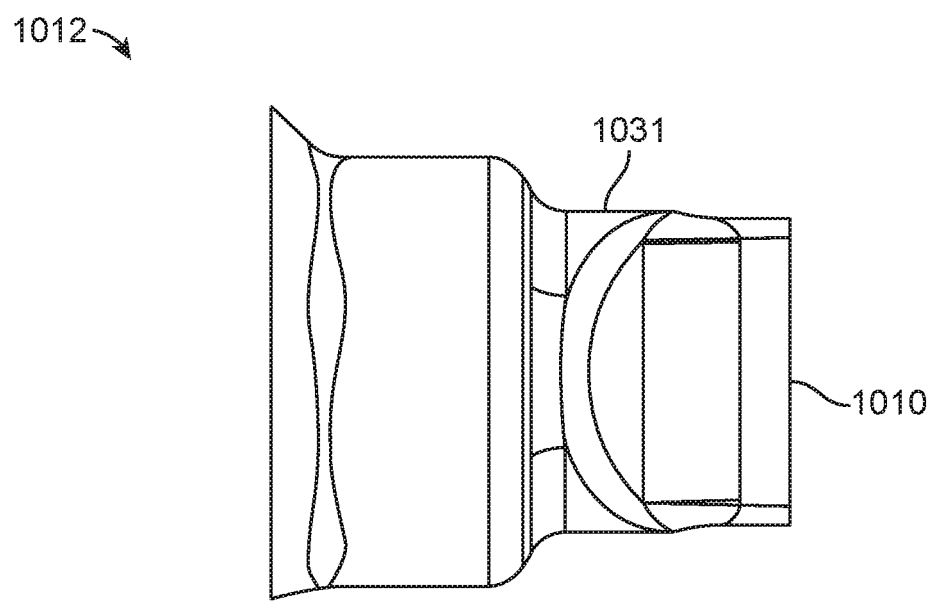
Figure 10E:
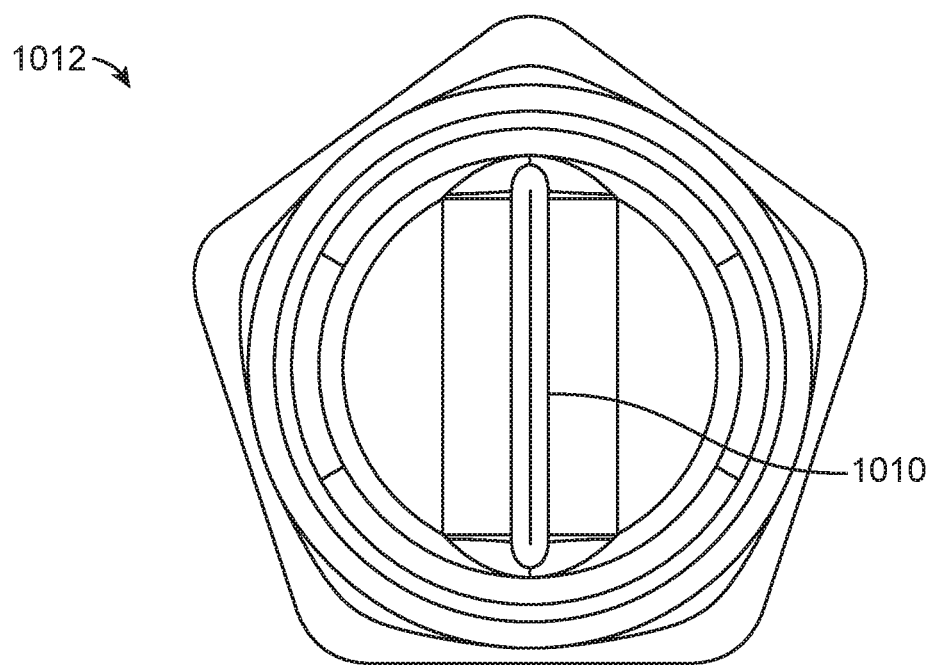
Figure 11A:
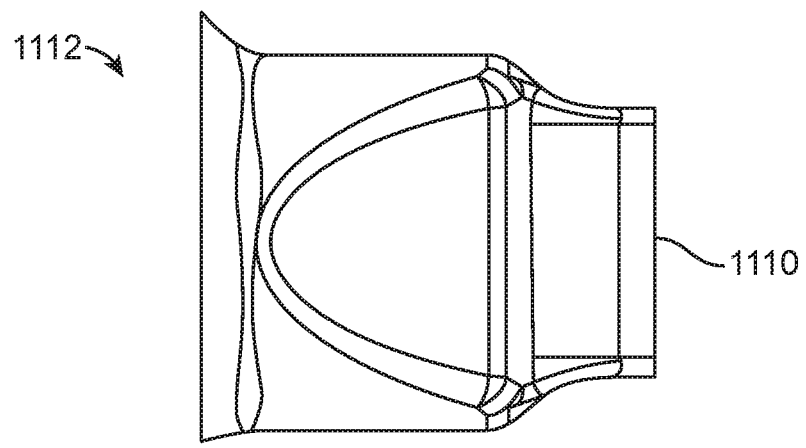
FIGS. 11A-E show an alternative duckbill valve with a cracking pressure above normal breathing pressures.
Figure 11B:
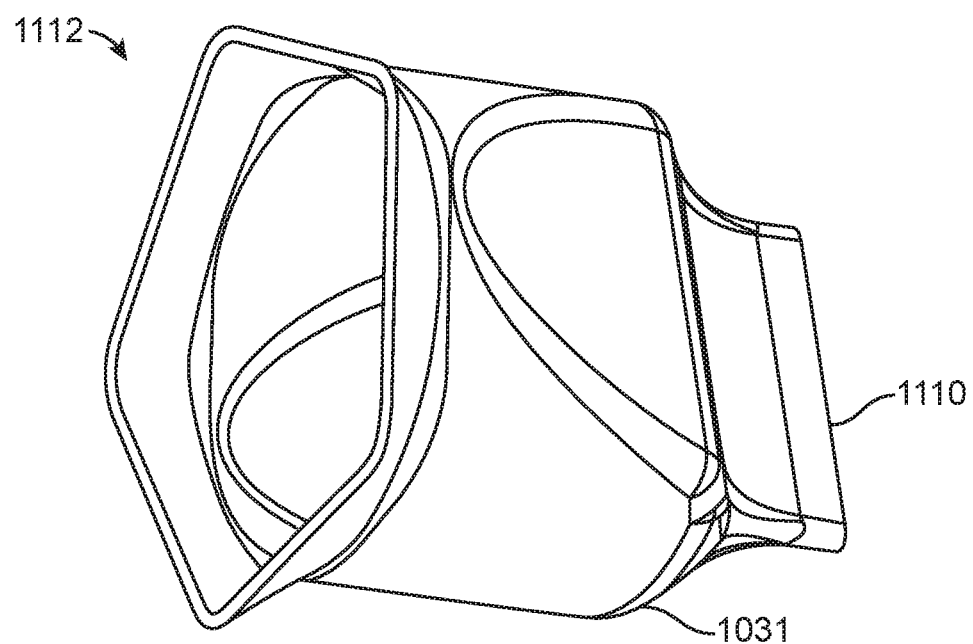
Figure 11C:
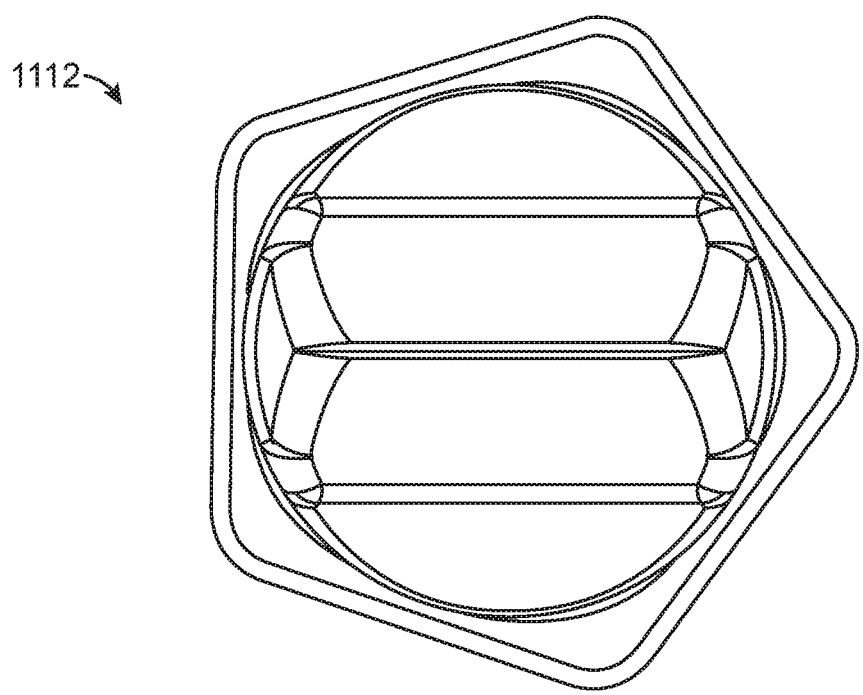
Figure 11D:
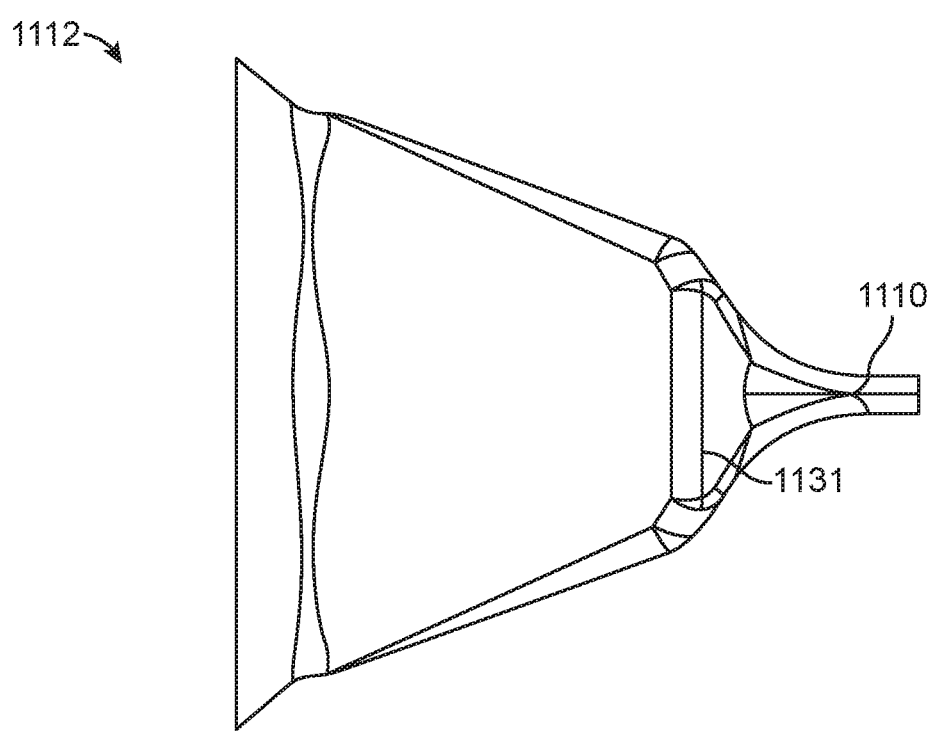
Figure 11E:
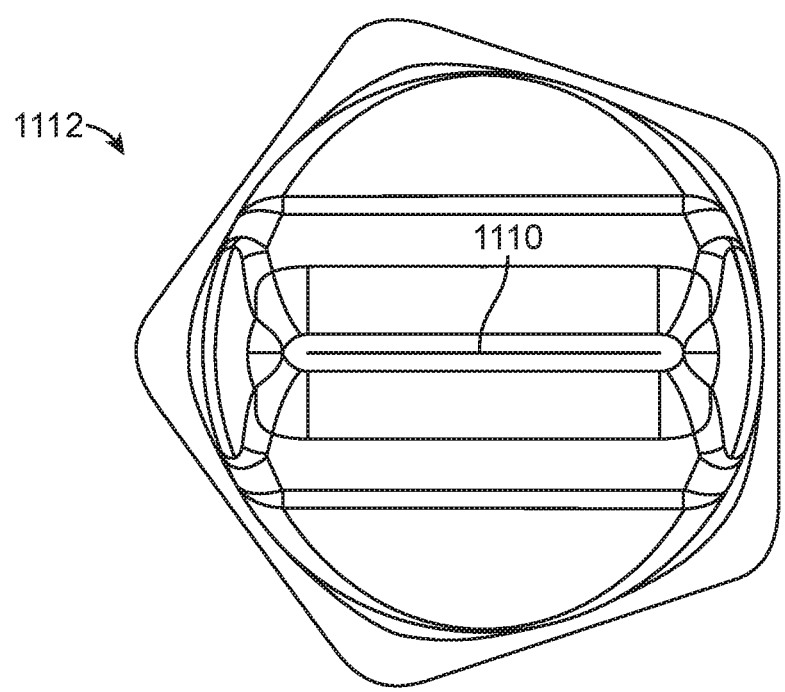
Figure 12A:
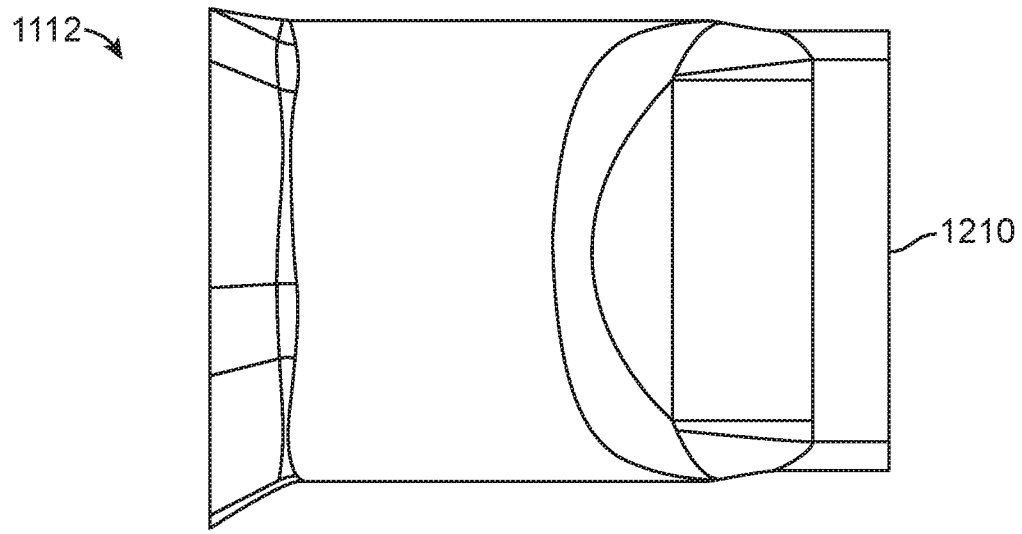
FIGS. 12A-E show an embodiment of a duckbill valve with a cracking pressure above normal breathing pressures.
Figure 12B:
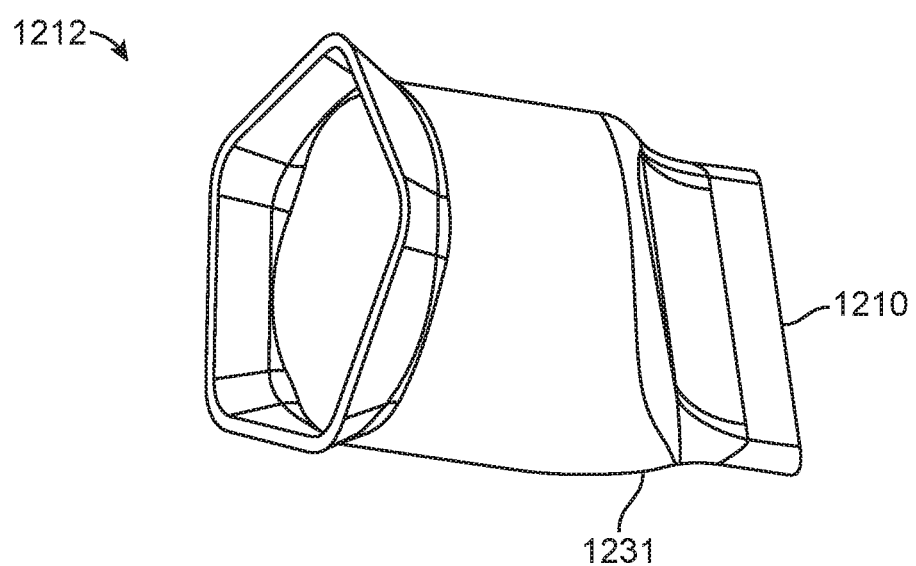
Figure 12C:
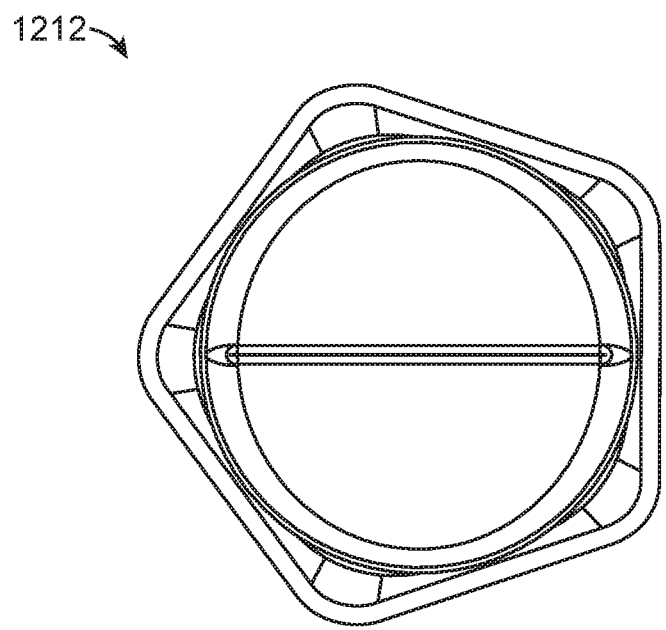
Figure 12D:
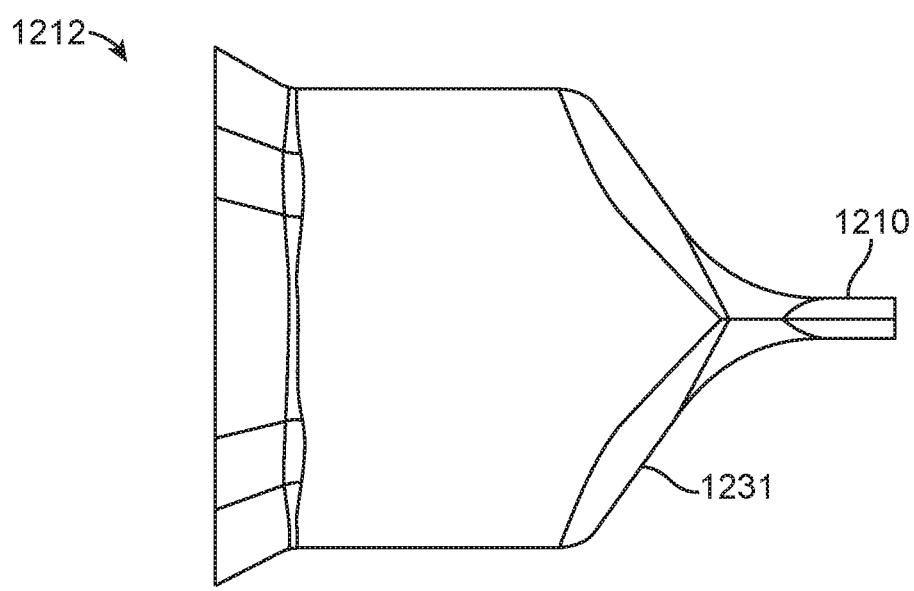
Figure 12E:
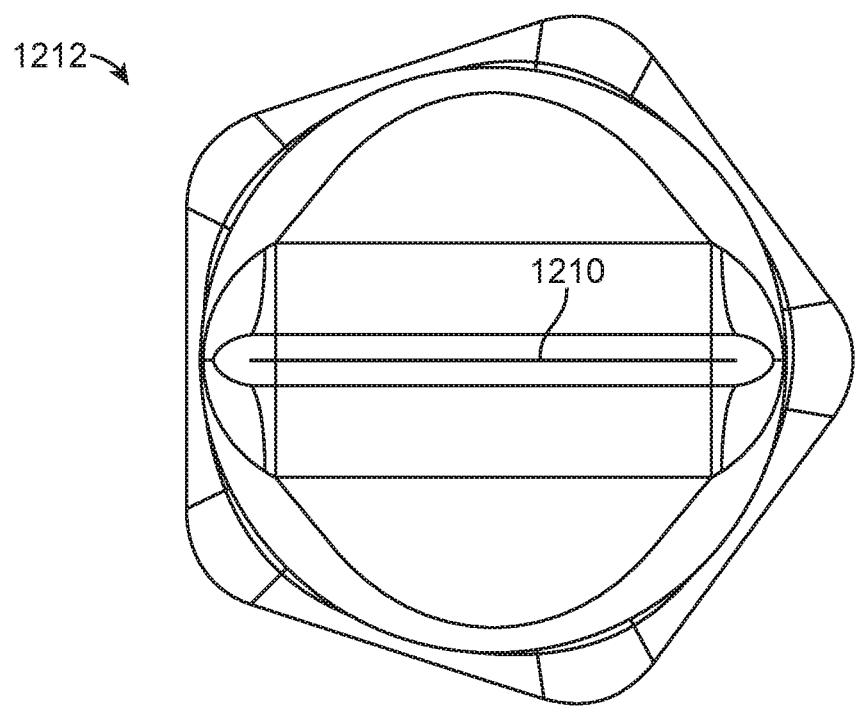

An example of a valve with a cracking pressure above normal breathing pressures is shown in FIG. 9. The valve 912 comprises a duckbill valve that includes two opposed, inclined walls or flaps 931 that are oriented at an angle 913 with respect to one another and lips 910 configured to be parallel with respect to one another in the closed configuration. The flaps 931 can open and close with respect to one another so as to form an opening between the lips 910. The relative positions of the lips 910 determines the size of the opening in the valve 912. When the lips 910 are in full contact with one another, there is no opening between the coaptation regions. In an embodiment, the inclined walls or flaps 931 are oriented at an angle relative to the longitudinal axis 905 of the valve while in the closed configuration. The lips may be configured to be parallel with the longitudinal axis 905 of the valve while in the closed configuration.

Various characteristics of the valve 912 may be varied to increase (or decrease) the cracking pressure of the valve 912. For example, the smaller the duckbill valve, the higher the cracking pressure that is generally required to open the valve. In addition, increasing the thickness 932 of a wall of the valve 912 will increase the cracking pressure. A longer parallel lip length 911 will also increase the cracking pressure of the valve 912. Increasing the angle 913 between the inclined walls or flaps 931 will increase the cracking pressure of the valve 912. In an embodiment, the angle 913 between the inclined walls or flaps 931 is in the range of approximately 70 to 110 degrees. The cracking pressure is also increased by orienting the valve 912 more orthogonal to the direction of flow. Additionally, the cracking pressure may be increased by narrowing the opening slit cut between the parallel lips 910.

FIGS. 10A-12E show various embodiments of valves with cracking pressures above normal breathing. The valves 1012, 1112, 1212 comprise inclined walls or flaps 1031, 1131, 1231 that are oriented at an angle with respect to one another and lips 1010, 1110, 1210 configured to be parallel with respect to one another in the closed configuration. The flaps 1031, 1131, 1231 can open and close with respect to one another so as to form an opening between the lips 1010, 1110, 1210. The relative positions of the lips 1010, 1110, 1210 determines the size of the opening in the valve 1012, 1112, 1212. When the lips 1010, 1110, 1210 are in full contact with one another, there is no opening between the coaptation regions.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A flow control device suitable for implanting in a bronchial passageway, comprising:
a valve element comprising a first lip, a second lip, and two opposed inclined flaps leading to the first and second lips, wherein the first and second lips are configured to transition the valve element between a closed configuration that blocks air flow in the inspiratory direction and an open configuration that permits air flow in an expiratory direction, wherein the first and second lips are configured to be parallel with respect to one another and a longitudinal axis of the valve and extend longitudinally in contact with one another beyond the two inclined flaps while in the closed configuration, and wherein the two inclined flaps are configured to be oriented at an angle with respect to one another in the closed configuration;
wherein a length of the parallel and contacted first and second lips extending longitudinally beyond the two inclined flaps and the angle of the inclined flaps with respect to one another are configured such that the valve element is in the closed configuration when exposed to no air flow, air flow in the inspiratory direction, and air flow in the expiratory direction at normal breathing pressures, and such that the valve element is in the open configuration when exposed to air flow in the expiratory direction at coughing pressures;
wherein the valve is configured to have a cracking pressure in the range of 12-24 inches $H_2O$.

2. The flow control device of claim 1, wherein the angle is in the range of 70 to 110 degrees.

3. The flow control device of claim 1, wherein the two inclined flaps are oriented at an angle relative to a longitudinal axis of the valve while in the closed configuration.

4. The flow control device of claim 1, further comprising a frame configured to retain the flow control device within the bronchial passageway; and a seal coupled to the frame, the seal configured to seal against internal walls of the bronchial passageway.

5. A flow control device suitable for implanting in a bronchial passageway, comprising:
a valve comprising coaptation regions comprising two opposed straight inclined flaps and two parallel lips connected to the straight inclined flaps, wherein the coaptation regions are configured to transition the valve element between a closed configuration that blocks air flow in the inspiratory direction and an open configuration that permits air flow in an expiratory direction, wherein the two opposed straight inclined flaps are configured to be oriented at an angle with respect to one another in the closed configuration, and the two parallel lips are configured to be parallel with respect to one another and a longitudinal axis of the valve and extend longitudinally in contact with one another beyond the two straight inclined flaps while in the closed configuration;
wherein a length of the parallel and contacted parallel lips extending longitudinally beyond the two straight inclined flaps and the angle of the straight inclined flaps with respect to one another are configured such that the coaptation regions are in the closed configuration when exposed to no air flow, air flow in the inspiratory direction, and air flow in the expiratory direction at normal breathing pressures, and such that the coaptation regions are in the open configuration when exposed to air flow in the expiratory direction at coughing pressures;
wherein the valve is configured to have a cracking pressure in the range of 12-24 inches $H_2O$.

6. The flow control device of claim 5, wherein the two opposed inclined flaps are configured to be oriented at an angle with respect to a longitudinal axis of the valve in the closed configuration.

7. The flow control device of claim 5, wherein the valve is configured to have a cracking pressure in the range of 15-24 inches $H_2O$.

8. The flow control device of claim 1, wherein the valve is configured to have a cracking pressure in the range of 15-24 inches $H_2O$.

9. The flow control device of claim 5, further comprising a frame configured to retain the flow control device within the bronchial passageway; and a seal coupled to the frame, the seal configured to seal against internal walls of the bronchial passageway.

10. The flow control device of claim 1, wherein the a valve element is configured to be oriented at an angle with respect to a direction of air flow through the bronchial passageway.

11. The flow control device of claim 5, wherein the a valve is configured to be oriented at an angle with respect to a direction of air flow through the bronchial passageway.

* * * * *